(12) United States Patent
Truitt et al.

(10) Patent No.: US 10,314,983 B2
(45) Date of Patent: Jun. 11, 2019

(54) STERILITY ENHANCED CLOSURE FOR A FLUID PATH

(71) Applicant: BAYER MEDICAL CARE INC., Indianola, PA (US)

(72) Inventors: Patrick W. Truitt, Mars, PA (US); Bernard J. Hobi, New Kensington, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 149 days.

(21) Appl. No.: 14/782,756

(22) PCT Filed: Mar. 28, 2014

(86) PCT No.: PCT/US2014/032116
§ 371 (c)(1),
(2) Date: Oct. 6, 2015

(87) PCT Pub. No.: WO2014/160911
PCT Pub. Date: Oct. 2, 2014

(65) Prior Publication Data
US 2016/0121054 A1 May 5, 2016

Related U.S. Application Data

(60) Provisional application No. 61/806,148, filed on Mar. 28, 2013.

(51) Int. Cl.
*A61M 5/32* (2006.01)
*A61M 5/31* (2006.01)

(52) U.S. Cl.
CPC ............ *A61M 5/3202* (2013.01); *A61M 5/31* (2013.01); *A61M 2005/312* (2013.01);
(Continued)

(58) Field of Classification Search
CPC .................. A61M 5/3202; A61M 5/31; A61M 2005/312; A61M 2005/3123;
(Continued)

(56) References Cited

U.S. PATENT DOCUMENTS 5,295,658 A * 3/1994 Atkinson ............ A61M 39/045
251/149.1
5,807,323 A 9/1998 Kriesel et al.
(Continued)

FOREIGN PATENT DOCUMENTS

WO 0172353 A2 10/2001

OTHER PUBLICATIONS

"Supplementary European Search Report from EP Application No. EP14774526", dated Oct. 17, 2016.
(Continued)

*Primary Examiner* — Bradley J Osinski
(74) *Attorney, Agent, or Firm* — Joseph L. Kent; David Schramm; James R. Stevenson

(57) ABSTRACT

A syringe assembly includes a syringe having a body with a proximal end and a distal end and a discharge outlet formed at the distal end of the syringe. The syringe assembly further includes a closure element having a body configured for removable engagement with at least a portion of the discharge outlet. The body of the closure element is porous to define a tortuous internal path through the body to allow venting of excess pressure within the syringe while preventing pathogens from entering the syringe. The discharge outlet is configured as a luer connector and the closure element has at least one engagement feature for engaging the luer connector.

14 Claims, 18 Drawing Sheets

(52) U.S. Cl.
CPC ............... *A61M 2005/3104* (2013.01); *A61M 2005/3106* (2013.01); *A61M 2005/3117* (2013.01); *A61M 2005/3123* (2013.01)

(58) Field of Classification Search
CPC .. A61M 2005/3106; A61M 2005/3104; A61M 2005/3117
See application file for complete search history.

(56) References Cited

U.S. PATENT DOCUMENTS

| | | | |
|---|---|---|---|
| 5,807,345 A | 9/1998 | Grabenkort | |
| 6,152,913 A * | 11/2000 | Feith | A61M 39/10 604/533 |
| 6,280,418 B1 * | 8/2001 | Reinhard | A61M 5/28 604/181 |
| 6,394,983 B1 | 5/2002 | Mayoral et al. | |
| 6,632,199 B1 * | 10/2003 | Tucker | A61M 5/3134 604/192 |
| 7,214,214 B2 * | 5/2007 | Sudo | A61M 5/3134 604/199 |
| 7,367,964 B2 | 5/2008 | Heinz et al. | |
| 2007/0078394 A1 * | 4/2007 | Gillespie, III | A61M 5/2033 604/134 |
| 2014/0188089 A1 * | 7/2014 | Midgette | A61M 39/16 604/539 |

OTHER PUBLICATIONS

International Preliminary Report on Patentability and Written Opinion dated Sep. 4, 2015.
"International Search Report from PCT/US2014/032116 dated Sep. 4, 2014".

* cited by examiner

STERILITY ENHANCED CLOSURE FOR A FLUID PATH

CROSS-REFERENCE TO RELATED APPLICATIONS

The present application is a U.S. national stage filing under 35 U.S.C. § 371 of International Application No. PCT/US2014/032116, filed Mar. 28, 2014, which claims priority to the Provisional U.S. Patent Application No. 61/806,148, entitled "Sterility Enhanced Closure for a Fluid Path" and filed on Mar. 28, 2013, the disclosures of each of which are incorporated herein by reference in their entirety.

BACKGROUND OF THE DISCLOSURE

Field of the Disclosure

The present disclosure is related to the medical field and, more particularly, to disposable syringes and removable sterile closures therefore used in the medical field, wherein the sterile closure is provided on the syringe during packaging, shipment, and storage of the syringe, and is then removed prior to use of the syringe.

Description of Related Art

Federal Food and Drug Administration (FDA) regulations require that the fluid path of a disposable syringe for administering therapeutic and diagnostic fluids to a patient be maintained in a sterile condition during shipment and storage of the syringe prior to its use. The conventional technique for maintaining the sterility of the fluid path is to enclose at least the portion of the syringe containing the fluid path in a blister pack seal with an indicating means, such as a foil label or sealing member, indicating the integrity of the seal. However, such blister packs are costly to produce and apply to the syringe during packaging. Further, a blister pack does not particularly conform to the structure of the syringe or the fluid path and, as such, is subject to damage and loss of seal during shipment and storage.

Within the prior art, a variety of alternative methods and devices for enclosing at least a portion of the syringe prior to its use have been developed. For example, U.S. Pat. No. 5,807,345 to Grabenkort discloses a luer cap configured for removably connecting to a male luer fitting at a discharge outlet of a syringe. The luer cap has an annular collar with internal threads that cooperate with the syringe luer fitting.

U.S. Pat. No. 6,394,983 to Mayoral et al. is directed to a cap and luer connector arrangement for a discharge outlet of a syringe. The connector has an inner sleeve with an inner surface configured for sealingly engaging a nozzle of the syringe. The connector is heat set to the syringe during an autoclave operation to prevent reinstallation of the connector once removed.

U.S. Pat. No. 6,632,199 to Tucker et al. is directed to a syringe assembly that includes a plastic cap and the discharge outlet of the syringe. The cap engages a luer fitting on the syringe to create a tight, sealing interference fit between the cap and the syringe. The cap provides a seal at two different points on the syringe: around the outside of the luer collar and inside the luer opening.

U.S. Pat. No. 7,367,964 to Heinz et al. is directed to a syringe having an open free end enclosed by a cap. The cap engages the free end of the syringe by interacting with the internal thread of a syringe connection formed at the free end.

While a variety of methods and devices for enclosing at least a portion of the syringe prior to its use have been proposed in the prior art, it is difficult to provide a method and device that maintains sterility of the discharge outlet of the syringe and its surrounding structure in various applications and under a variety of circumstances. For example, existing cap designs do not allow for venting of pressure inside the syringe. Venting of the pressure inside the syringe is an important design consideration because excess pressure may cause the plunger to move from its desired initial position, such as its position when the syringe is pre-filled with a fluid. Designs that incorporate a venting feature are overly complex and prohibitively expensive to use. It would be advantageous to provide a sterility enhanced closure for a fluid path of a syringe that maintains sterility of various components at the discharge outlet of the syringe.

SUMMARY OF THE DISCLOSURE

The problem being solved by various embodiments discussed herein is that currently there are no known caps that can be readily and cost-effectively mated to the end of a syringe. In view of the existing shortcomings of the prior art, various embodiments discussed herein provide for a cost-effective closure element that may be conform to the configuration of the syringe and the fluid path in order to cover and protect the fluid path and provide a tortuous path to block the entry of pathogens while allowing the venting of pressure from the syringe. Various embodiments discussed herein ensure that the plunger of the syringe does not move due to changes in barometric pressure from thermal expansion or due to pressure buildup during an automatic advancement of a piston/plunger assembly in an automated injector when the closure element is still installed.

In accordance with one embodiment, a syringe assembly may include a syringe having a body with a proximal end and a distal end and a discharge outlet formed at the distal end of the syringe. The syringe assembly may further include a closure element having a body configured for removable engagement with at least a portion of the discharge outlet. The body of the closure element may be porous to define a tortuous internal path through the body to allow venting of excess pressure within the syringe while preventing pathogens from entering the syringe. The discharge outlet may be configured as a luer connector and the closure element has at least one engagement feature for engaging the luer connector. The engagement feature may be a crush rib or an annular ring configured to surround at least a portion of the luer connector. The body of the closure element may have at least one raised or recessed element to assist in grasping the closure element during removal of the closure element from the discharge outlet. The closure element may be made from a polypropylene material that is press-formed.

In accordance with another embodiment, a closure element for a discharge outlet of a syringe may include a body having a distal portion and a proximal portion configured for removable engagement with at least a portion of a discharge outlet of a syringe. The closure element may further include at least one engagement feature on the proximal portion for engaging the discharge outlet. The body may be porous to define a tortuous internal path through the body to allow venting of excess pressure within the syringe while preventing pathogens from entering the syringe. The engagement feature may be a crush rib or an annular ring configured to surround at least a portion of the discharge outlet. The closure element may further include a vent extending through at least a portion of the body to allow venting of excess pressure within the syringe while preventing pathogens from entering the syringe. The body of the closure element may have at least one raised or recessed element to assist in grasping the closure element during removal of the closure element from a discharge outlet of the syringe. The closure element may be made from a polypropylene material that is press-formed.

In accordance with another embodiment, a closure element for a discharge outlet of a syringe may include a body having a distal portion and a proximal portion configured for removable engagement with at least a portion of a discharge outlet of a syringe. The proximal portion may have a substrate made from a first material and a jacket made from a second material. The first material may be different from the second material. The jacket may be molded over the substrate to envelop at least a portion of the substrate. A vent may be provided such that the vent extends through at least a portion of the body to allow venting of excess pressure within the syringe while preventing pathogens from entering the syringe. The closure element may be made from a polypropylene material that is press-formed.

Further details and advantages of the various embodiments described in detail herein will become clear upon reviewing the following detailed description of the various embodiments in conjunction with the accompanying drawing figures.

DETAILED DESCRIPTION OF THE DISCLOSURE

Figure 1A:
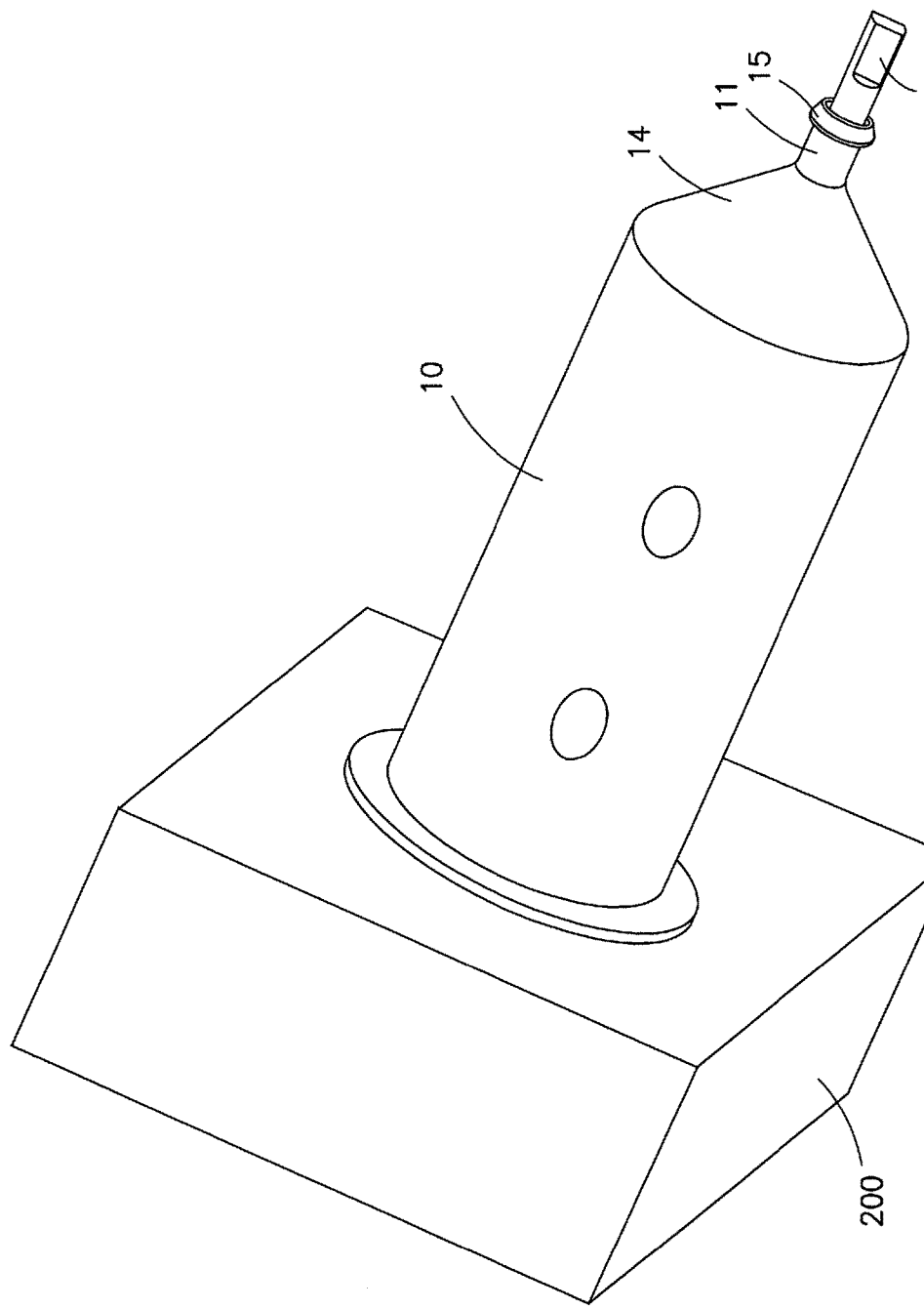
FIG. 1A is a perspective view of a syringe with a sterility enhanced closure element in accordance with one embodiment.

The illustrations generally show preferred and non-limiting embodiments of the systems and methods of the present disclosure. While the descriptions present various embodiments of the devices, it should not be interpreted in any way as limiting the disclosure. Furthermore, modifications, concepts, and applications of the disclosure's embodiments are to be interpreted by those skilled in the art as being encompassed, but not limited to, the illustrations and descriptions herein.

The following description is provided to enable those skilled in the art to make and use the described embodiments contemplated for carrying out the disclosure. Various modifications, equivalents, variations, and alternatives, however, will remain readily apparent to those skilled in the art. Any and all such modifications, variations, equivalents, and alternatives are intended to fall within the spirit and scope of the present disclosure.

Further, for purposes of the description hereinafter, the terms "end", "upper", "lower", "right", "left", "vertical", "horizontal", "top", "bottom", "lateral", "longitudinal", and derivatives thereof shall relate to the disclosure as it is oriented in the drawing figures. The term "proximal" refers to the direction toward the center or central region of the device. The term "distal" refers to the outward direction extending away from the central region of the device. However, it is to be understood that the disclosure may assume various alternative variations and step sequences, except where expressly specified to the contrary. It is also to be understood that the specific devices and processes illustrated in the attached drawings, and described in the following specification, are simply exemplary embodiments of the disclosure. Hence, specific dimensions and other physical characteristics related to the embodiments disclosed herein are not to be considered as limiting. For the purpose of facilitating understanding of the disclosure, the accompanying drawings and description illustrate preferred embodiments thereof, from which the disclosure, various embodiments of its structures, construction and method of operation, and many advantages may be understood and appreciated.

Figure 1B:
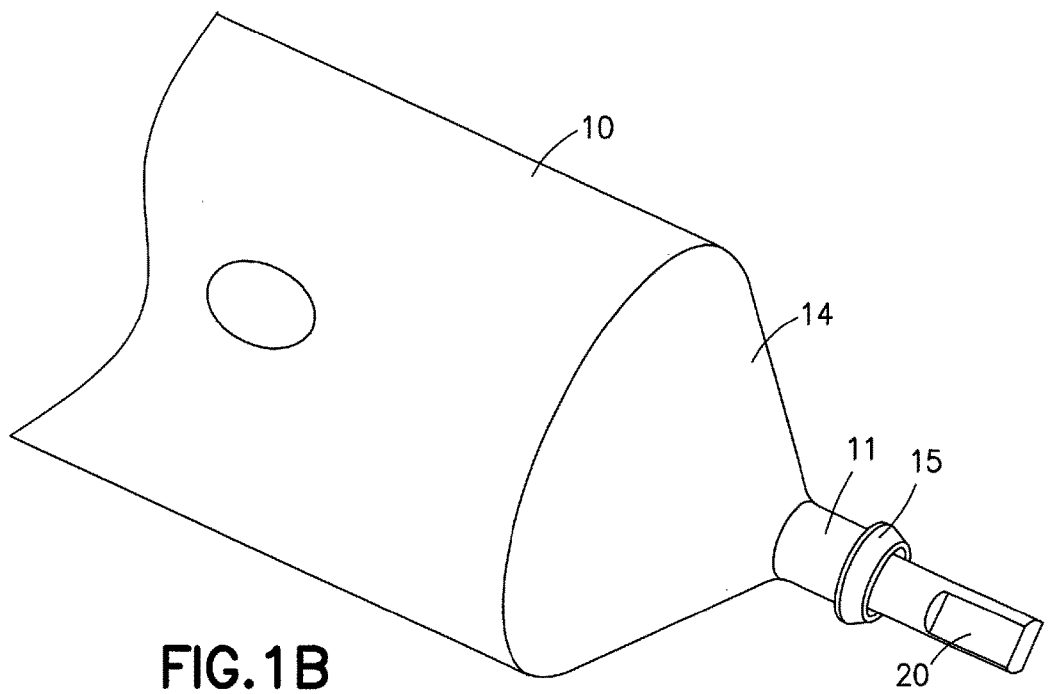
FIG. 1B is an enlarged perspective view of a distal portion of the syringe shown in FIG. 1A with a detailed view of the closure element.

FIGS. 1A and 1B illustrate a syringe 10 in accordance with an embodiment of the present disclosure. The syringe 10 includes a tubular body with a proximal end 13 and a distal end 14. The proximal end 13 of the syringe 10 is configured for interaction with a fluid injector 200, where the syringe plunger (not shown) is acted upon by a drive member (not shown) of the injector 200. The tubular body of the syringe 10 is configured for receiving fluid therein, which is discharged from the syringe body through a discharge outlet 11 surrounding a fluid path 12 (shown in FIG. 2B) provided at the distal end 14 of the syringe 10. The discharge outlet 11 includes a connector 15 (shown in FIG. 2B) monolithically formed with the body of the syringe 10. The connector 15 may be a luer-lock connector that includes a central passage 16 with an annular skirt 17 surrounding the central passage 16. The annular skirt 17 has threads 18 on its interior side for engaging external threads of a mating connection. The fluid path 12 extends through the central passage 16.

A closure element 20, which is made in accordance with any one of several embodiments of the present disclosure to be discussed below, is at least partially positioned within the discharge outlet 11 of the syringe 10 in order to maintain the sterility of a fluid path 12 (shown in FIG. 2B) positioned within the discharge outlet 11.

Figure 2A:
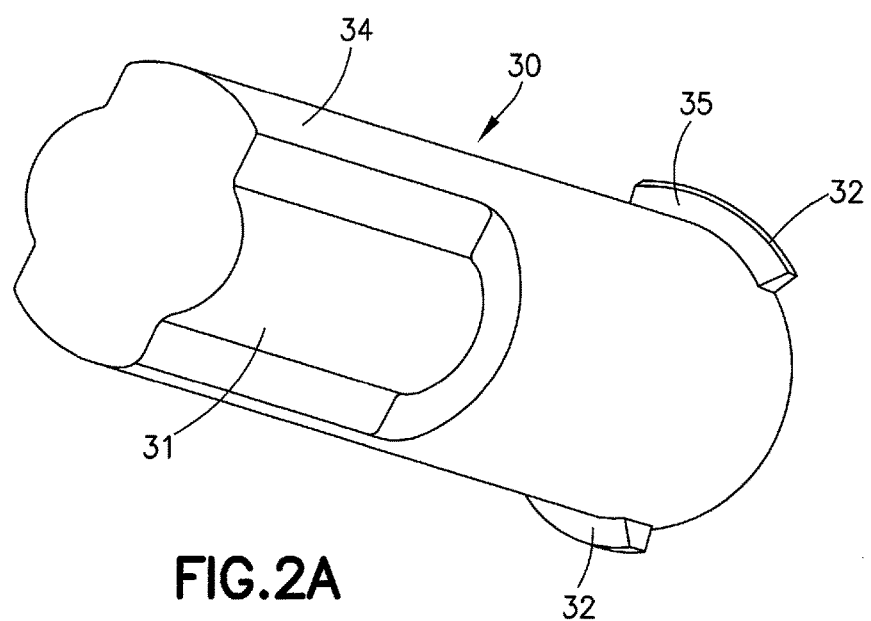
FIG. 2A is a perspective view of a sterility enhanced closure element in accordance with another embodiment.
Figure 2B:
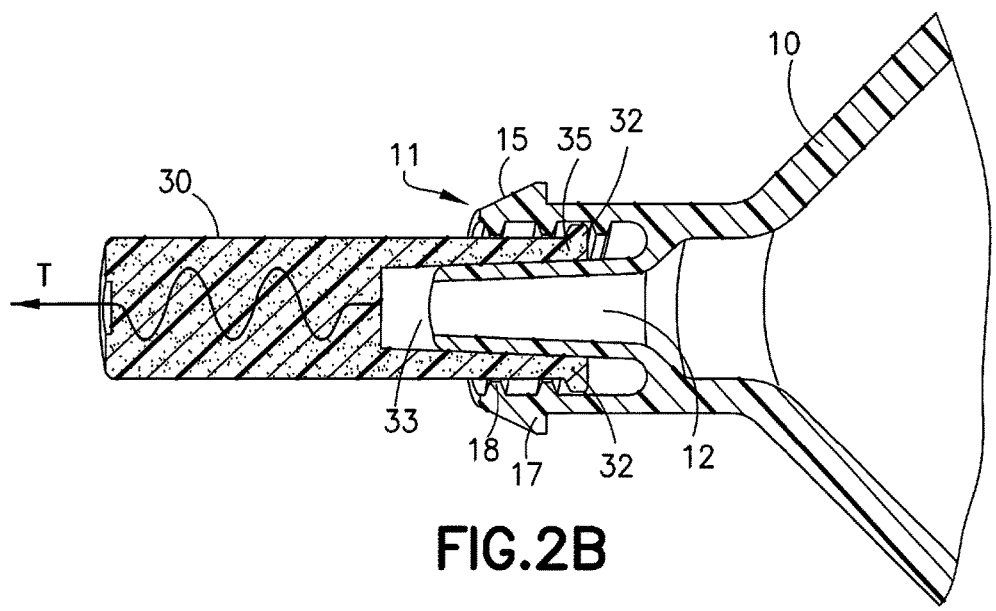
FIG. 2B is a cross-sectional view of the sterility enhanced closure element shown in FIG. 2A in use with a syringe.

FIGS. 2A and 2B illustrate a closure element 30 in accordance with an embodiment of the present disclosure. The closure element 30 includes a body 34 having one or more recessed features 31 molded therein to assist in grasping the closure element 30 for removal from the discharge outlet 11 of the syringe 10. Alternatively, the recessed features 31 may be formed as protrusions that extend radially outward from the body 34. In either embodiment, the recessed features 31 provide a grasping surface to facilitate the removal of the closure element 30 from the discharge outlet 11 of the syringe 10. The recessed features 31, and/or the surface surrounding the recessed features 31, may be textured to provide an increased frictional interface with the user's fingers during removal of the closure element 30.

As shown in FIG. 2B, the closure element 30 is at least partially positioned within the discharge outlet 11 such that the closure element 30 is configured for engagement with the connector 15. The closure element 30 includes an internal cavity 33 formed therein. The internal cavity 33 receives a fluid path 12 of the syringe 10. In particular, the internal cavity 33 is shaped to receive the central passage 16 through which the fluid path 12 extends. The external surface of the closure element 30 includes at least two male threads 35 that are configured for engaging the female thread 18 of the annular skirt 17 of the connector 15.

Figure 2C:
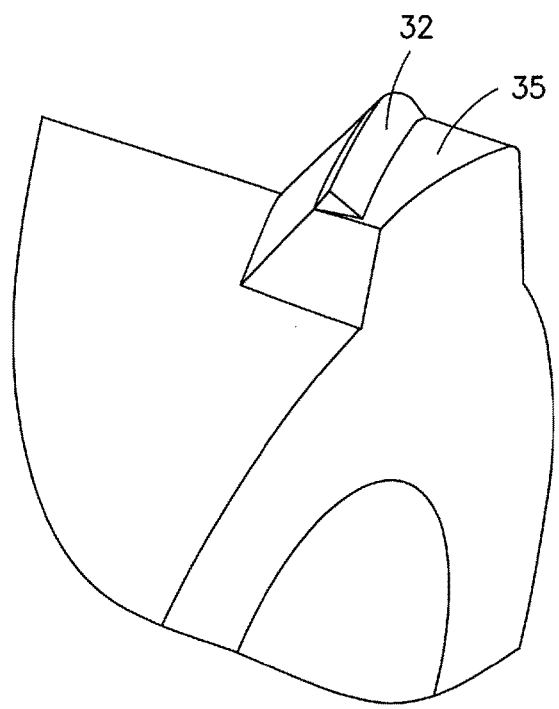
FIG. 2C is a detailed view of a crush rib of the sterility enhanced closure element.
Figure 3A:
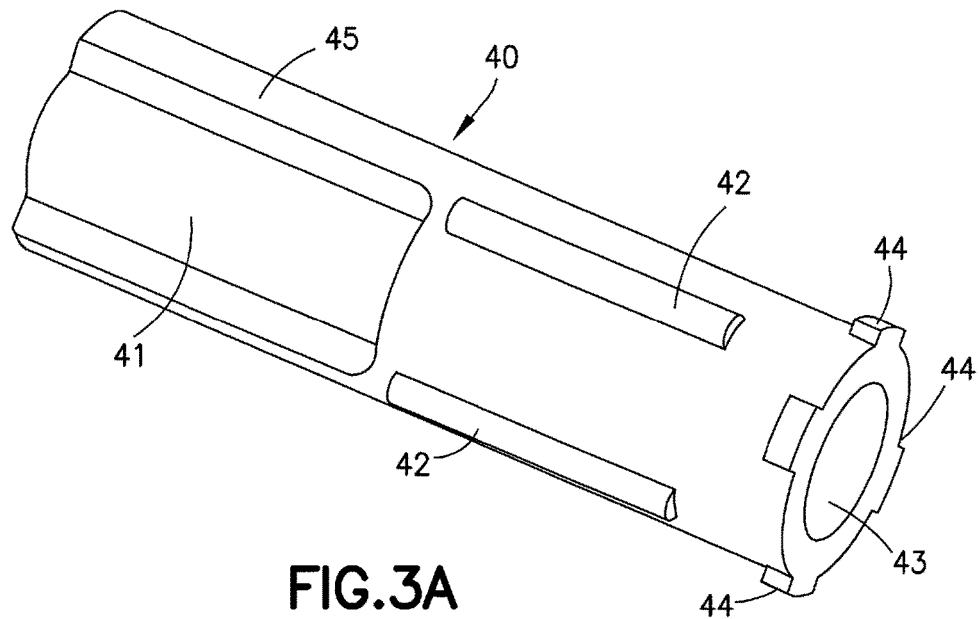
FIG. 3A is a perspective view of a sterility enhanced closure element in accordance with another embodiment.
Figure 3B:
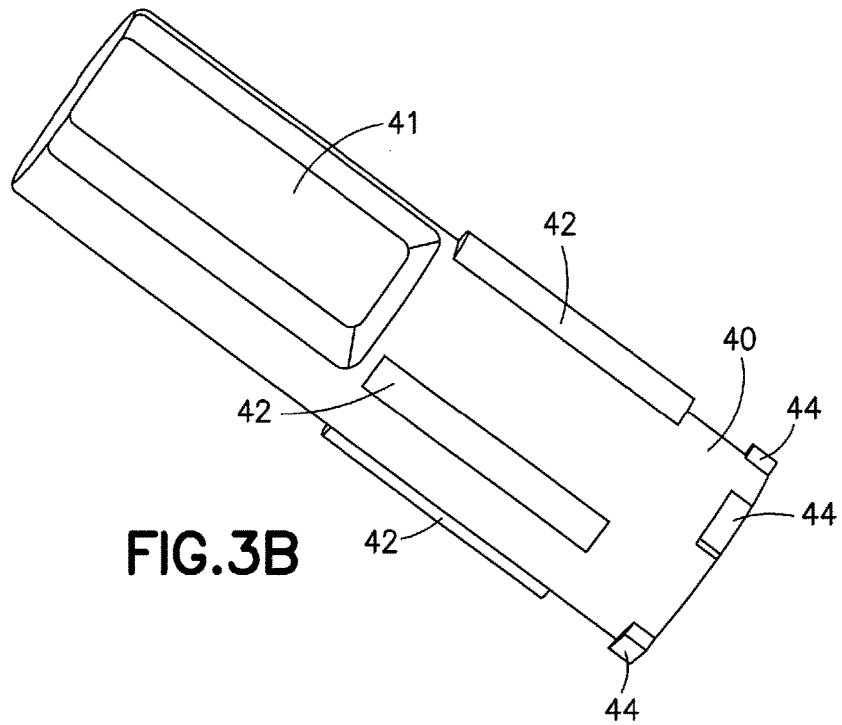
FIG. 3B is a side view of the closure element shown in FIG. 3A.
Figure 3C:
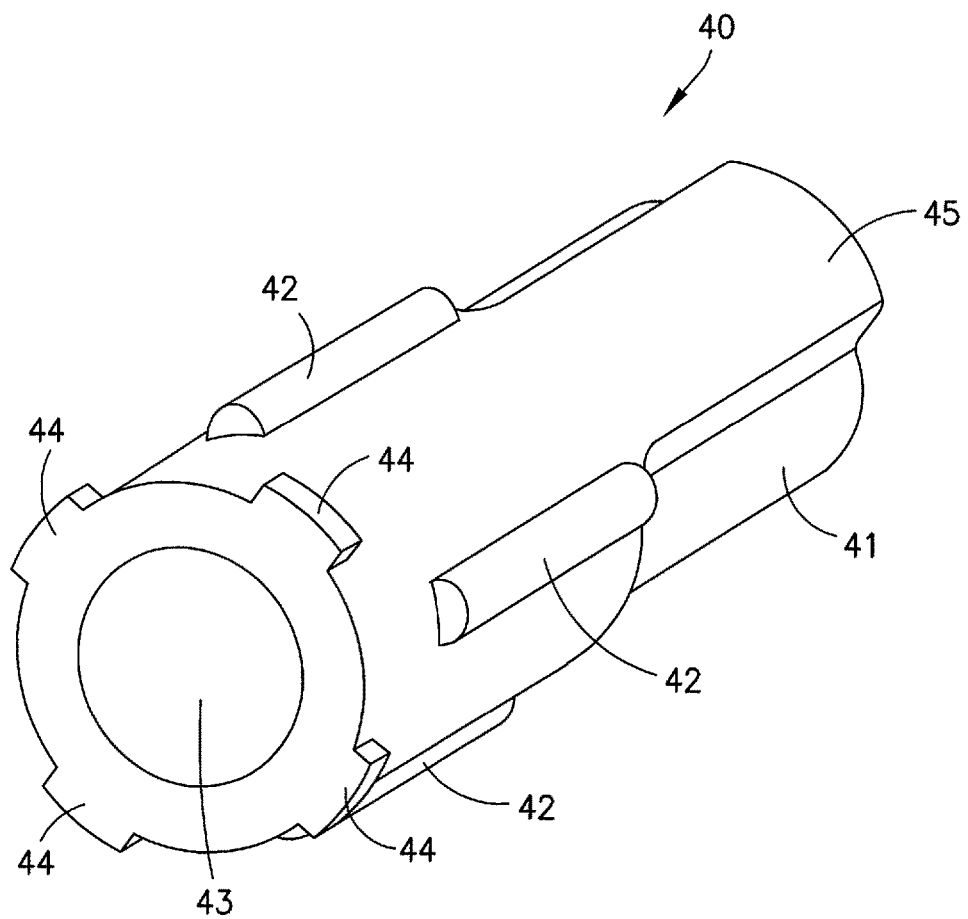
FIG. 3C is a perspective view of a proximal end of the closure element shown in FIG. 3A.
Figure 3D:
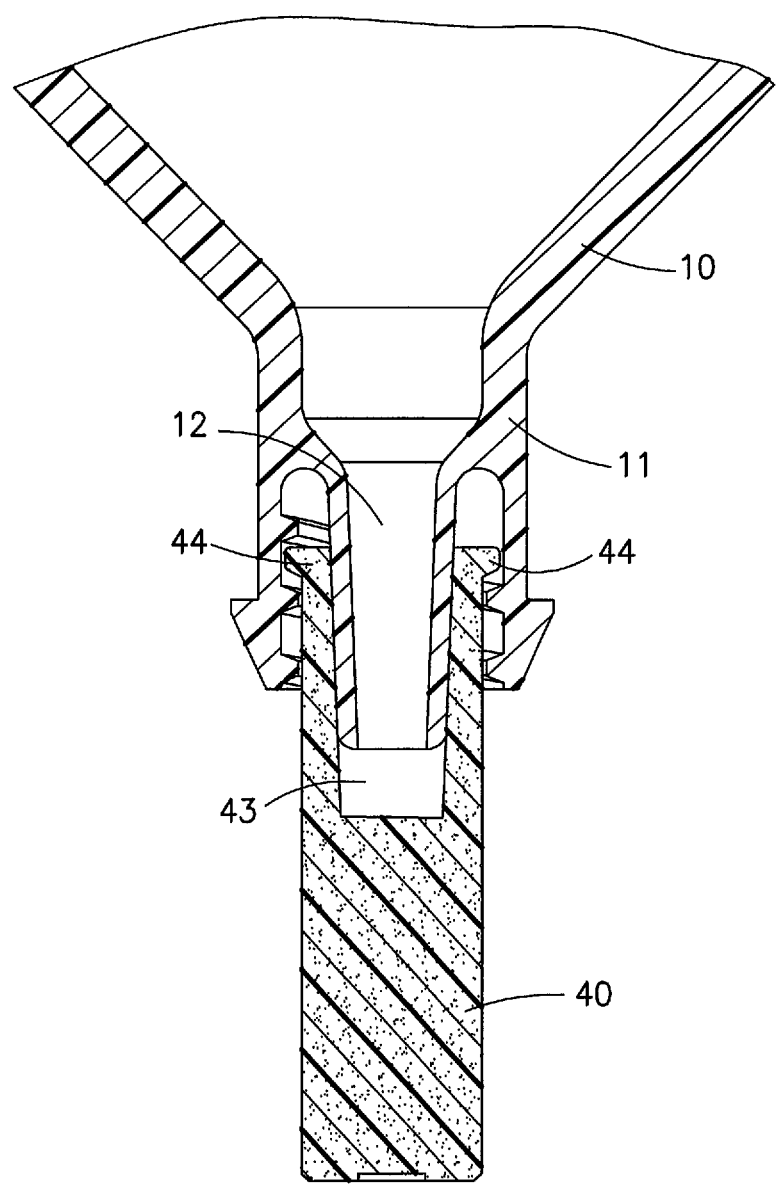
FIG. 3D is a cross-sectional view of the sterility enhanced closure element shown in FIG. 3A in use with a syringe.
Figure 4A:
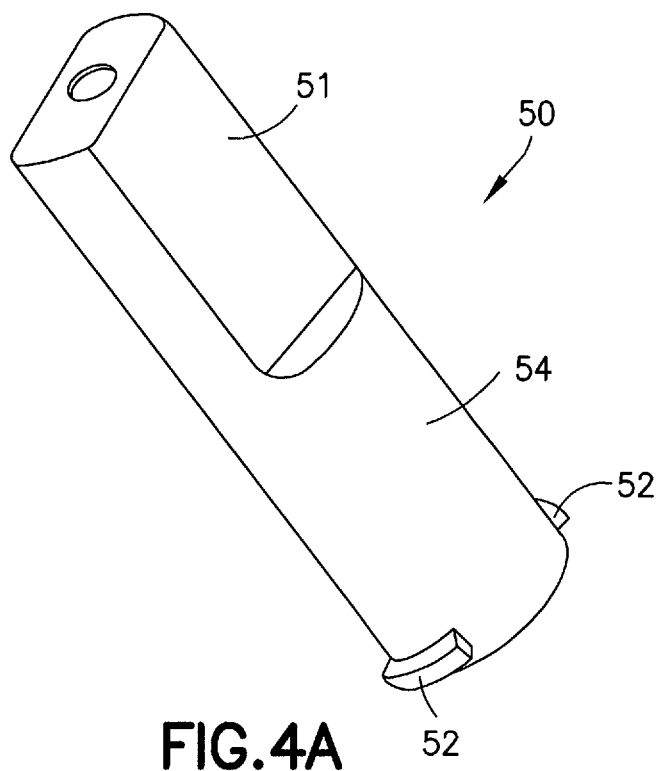
FIG. 4A is a perspective view of a sterility enhanced closure element in accordance with another embodiment.
Figure 4B:
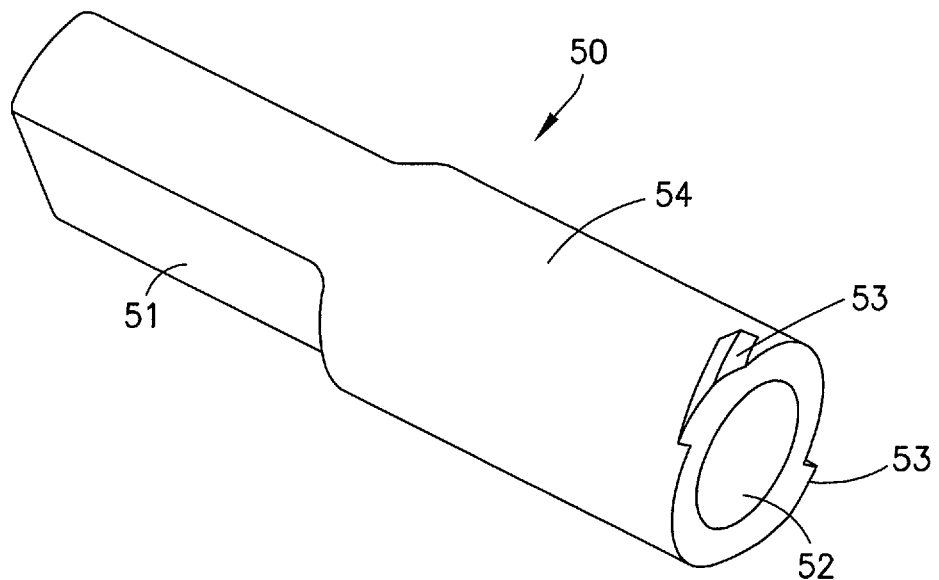
FIG. 4B is a perspective view of a proximal end of the closure element shown in FIG. 4A.
Figure 4C:
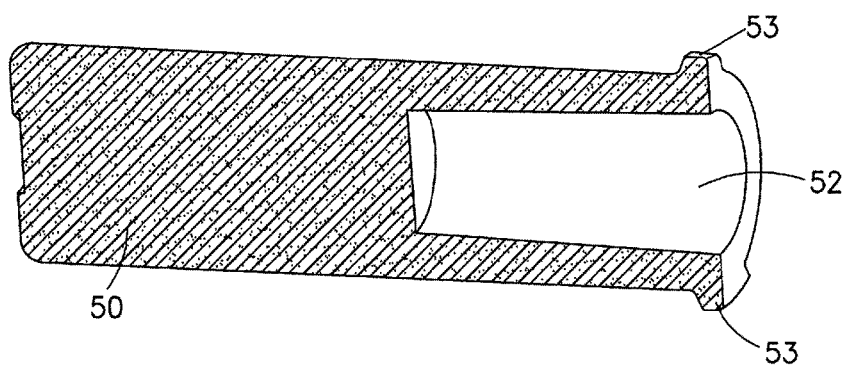
FIG. 4C is a cross-sectional view of the closure element shown in FIG. 4A.
Figure 4D:
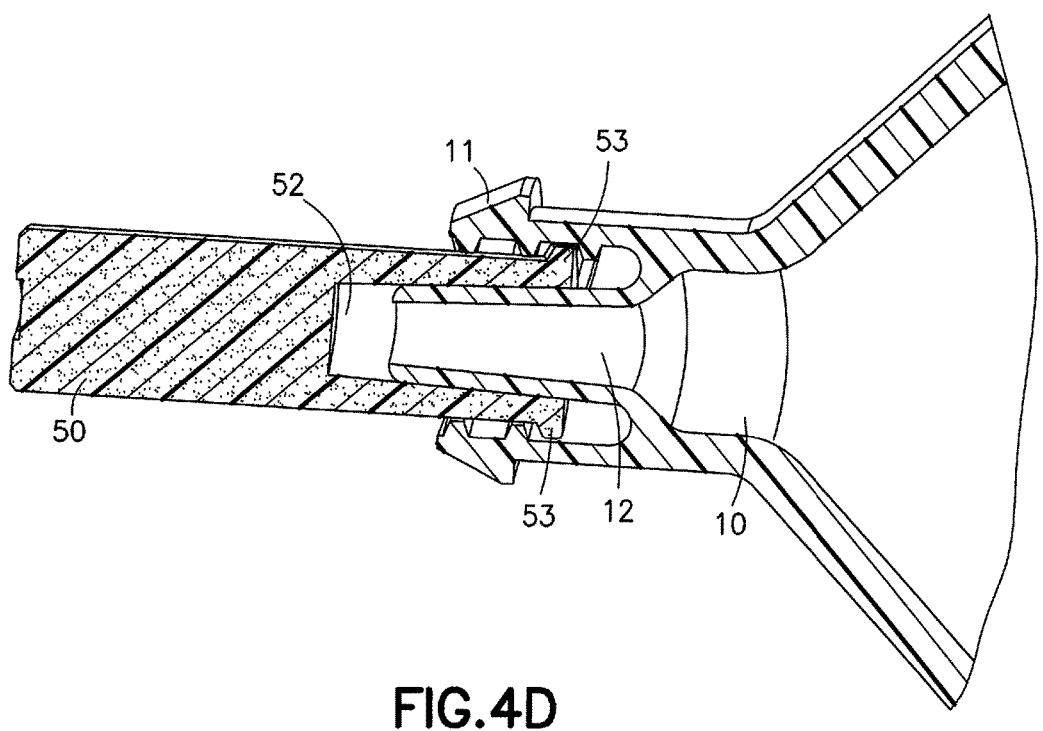
FIG. 4D is a cross-sectional view of the sterility enhanced closure element shown in FIG. 4A in use with a syringe.

As shown in FIGS. 2B-2C, the male threads 35 of closure element 30 may also include at least two crush ribs 32 extending radially outward from the male threads 35. The crush ribs 32 are configured to engage the threads 18 of the connector 15 to create a mechanical and frictional engagement between the closure element 30 and the discharge outlet 11 in order to prevent accidental removal or displacement of the closure element 30.

The closure element 30 is made from a press-formed polyethylene material that is made porous, such that air is able to pass through the body of the closure element 30 but a tortuous path T is formed that prevents passage of pathogens through the closure element 30, thereby maintaining the sterility of the fluid path 12. The use of a porous material, such as the press-formed polyethylene material, forms a complex inner geometry of the body 34 to allow venting of excess pressure within the syringe. The inner geometry of the body 34 is also tortuous enough to prevent pathogens from entering the fluid path 12 and compromising the sterility of the connection. By venting the excess pressure built up within the body of the syringe 10, the closure element 30 ensures that the plunger of the syringe 10 does not move due to changes in barometric pressure from thermal expansion or due to pressure buildup during an automatic advancement of a piston/plunger assembly in an automated fluid injector when the closure element 30 is still installed. The closure element 30 may be left on the syringe 10 while the syringe 10 is loaded in the fluid injector and the auto forward function is engaged to maintain the sterility of the discharge outlet 11 at all times prior to removing the closure element 30 and connecting the discharge outlet 11 with a patient fluid path set.

FIGS. 3A-3D illustrate a closure element 40 in accordance with another embodiment of the present disclosure. The closure element 40 includes a body 45 having recessed features 41 molded therein to assist in grasping the closure element 40 for removal from the discharge outlet 11 of the syringe 10 (shown in FIG. 3D). Alternatively, the recessed features 41 may be formed as protrusions that extend radially outward from the body 45. In either embodiment, the recessed features 41 provide a grasping surface to facilitate the removal of the closure element 40 from the discharge outlet 11 of the syringe 10. The recessed features 41, and/or the surface surrounding the recessed features 41, may be textured to provide an increased frictional interface with the user's fingers during removal of the closure element 40.

The closure element 40 may also include a plurality of ribs 42, which serve to structurally strengthen the closure element 40. The closure element 40 is at least partially positioned within the discharge outlet 11 such that the closure element 40 is configured for engagement with the connector 15. The closure element 40 includes an internal cavity 43 formed therein. The internal cavity 43 receives a fluid path 12 of the syringe 10. In particular, the internal cavity 43 is shaped to receive the central passage 16 through which the fluid path 12 extends.

With continuing reference to FIGS. 3A-3D, the closure element 40 may also include at least four crush ribs 44 extending radially outward from the body 45 of the closure element 40. The crush ribs 44 are configured to engage the threads 18 of the connector 15 to create a mechanical and frictional engagement between the closure element 40 and the discharge outlet 11 in order to prevent accidental removal or displacement of the closure element 40.

The closure element 40 is made from a press-formed polyethylene material that is made porous, such that air is able to pass through the body of the closure element 40 but a tortuous path is formed that prevents passage of pathogens through the closure element 40, thereby maintaining the sterility of the fluid path 12. The use of a porous material, such as the press-formed polyethylene material, forms a complex inner geometry of the body 45 to allow venting of excess pressure within the syringe. The inner geometry of the body 45 is also tortuous enough to prevent pathogens from entering the fluid path 12 and compromising the sterility of the connection. By venting the excess pressure built up within the body of the syringe 10, the closure element 40 ensures that the plunger of the syringe 10 does not move due to changes in barometric pressure from thermal expansion or due to pressure buildup during an automatic advancement of a piston/plunger assembly in an automated fluid injector when the closure element 40 is still installed. The closure element 40 may be left on the syringe 10 while the syringe 10 is loaded in the fluid injector and the auto forward function is engaged to maintain the sterility of the discharge outlet 11 at all times prior to removing the closure element 40 and connecting the discharge outlet 11 with a patient fluid path set.

FIGS. 4A-4D illustrate a closure element 50 in accordance with another embodiment of the present disclosure. The closure element 50 includes a body 54 having recessed features 51 molded therein to assist in grasping the closure element 50 for removal from the discharge outlet 11 of the syringe 10. Alternatively, the recessed features 51 may be formed as protrusions that extend radially outward from the body 54. In either embodiment, the recessed features 51 provide a grasping surface to facilitate the removal of the closure element 50 from the discharge outlet 11 of the syringe 10. The recessed features 51, and/or the surface surrounding the recessed features 51, may be textured to provide an increased frictional interface with the user's fingers during removal of the closure element 50.

The closure element 50 is at least partially positioned within the discharge outlet 11 such that the closure element 50 is configured for engagement with the connector 15. The closure element 50 includes an internal cavity 52 formed therein. The internal cavity 52 receives a fluid path 12 of the syringe 10. In particular, the internal cavity 52 is shaped to receive the central passage 16 through which the fluid path 12 extends.

As shown in FIGS. 4A-4D, the closure element 50 may also include at least two crush ribs 53 extending radially outward from the body 54 of the closure element 50. The crush ribs 53 are configured to engage the threads 18 of the connector 15 to create a mechanical and frictional engagement between the closure element 50 and the discharge outlet 11 in order to prevent accidental removal or displacement of the closure element 50.

The closure element 50 is made from a press-formed polyethylene material that is made porous, such that air is able to pass through the body of the closure element 50 but a tortuous path is formed that prevents passage of pathogens through the closure element 50, thereby maintaining the sterility of the fluid path 12. The use of a porous material, such as the press-formed polyethylene material, forms a complex inner geometry of the body 54 to allow venting of excess pressure within the syringe. The inner geometry of the body 54 is also tortuous enough to prevent pathogens from entering the fluid path 12 and compromising the sterility of the connection. By venting the excess pressure built up within the body of the syringe 10, the closure element 50 ensures that the plunger of the syringe 10 does not move due to changes in barometric pressure from thermal expansion or due to pressure buildup during an automatic advancement of a piston/plunger assembly in an automated fluid injector when the closure element 50 is still installed. The closure element 50 may be left on the syringe 10 while the syringe 10 is loaded in the fluid injector and the auto forward function is engaged to maintain the sterility of the discharge outlet 11 at all times prior to removing the closure element 50 and connecting the discharge outlet 11 with a patient fluid path set.

Figure 5A:
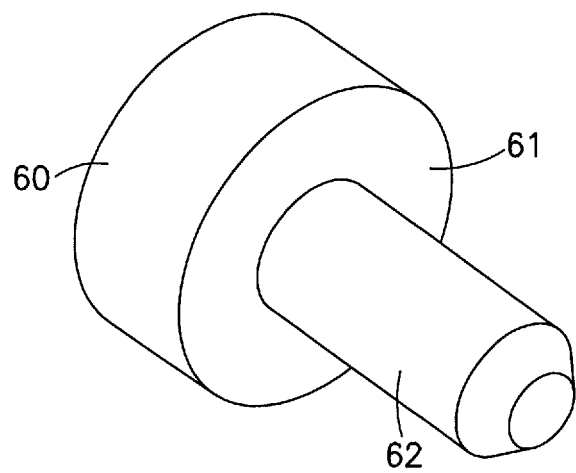
FIG. 5A is a perspective view of a sterility enhanced closure element in accordance with another embodiment.
Figure 5B:
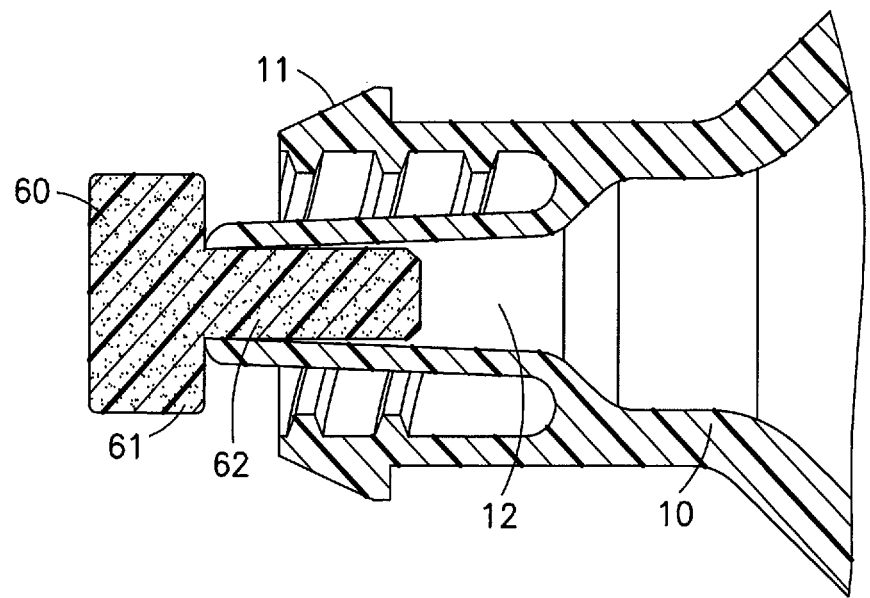
FIG. 5B is a cross-sectional view of the sterility enhanced closure element shown in FIG. 5A in use with a syringe.

FIGS. 5A and 5B, illustrate a closure element 60 in accordance with another embodiment of the present disclosure. The closure element 60 includes a body configured in a form analogous to a push pin with an enlarged distal portion 61, which is disposed outside of the discharge outlet 11 of the syringe 10, and a proximal portion 62. The distal portion 61 is configured to be grasped to remove the closure element 60 from the discharge outlet 11. The proximal portion 62 is configured to be received within the fluid path 12 in an interference fit such that the closure element 60 covers and plugs the fluid path 12 to protect the fluid path 12 and to prevent accidental removal or displacement of the closure element 60.

The closure element 60 is made from a press-formed polyethylene material that is made porous such that air is able to pass through the body of the closure element, but a tortuous path is formed that prevents passage of pathogens through the closure element 60 and the sterility of the fluid path is maintained. The use of a porous material, such as the press-formed polyethylene material, forms a complex inner geometry of the closure element 60 to allow venting of excess pressure within the syringe. The inner geometry of the closure element 60 is also tortuous enough to prevent pathogens from entering the fluid path 12 and compromising the sterility of the connection. By venting the excess pressure built up within the body of the syringe 10, the closure element 60 ensures that the plunger of the syringe 10 does not move due to changes in barometric pressure from thermal expansion or due to pressure buildup during an automatic advancement of a piston/plunger assembly in an automated fluid injector when the closure element 60 is still installed. The closure element 60 may be left on the syringe 10 while the syringe 10 is loaded in the fluid injector and the auto forward function is engaged to maintain the sterility of the discharge outlet 11 at all times prior to removing the closure element 60 and connecting the discharge outlet 11 with a patient fluid path set.

Figure 6A:
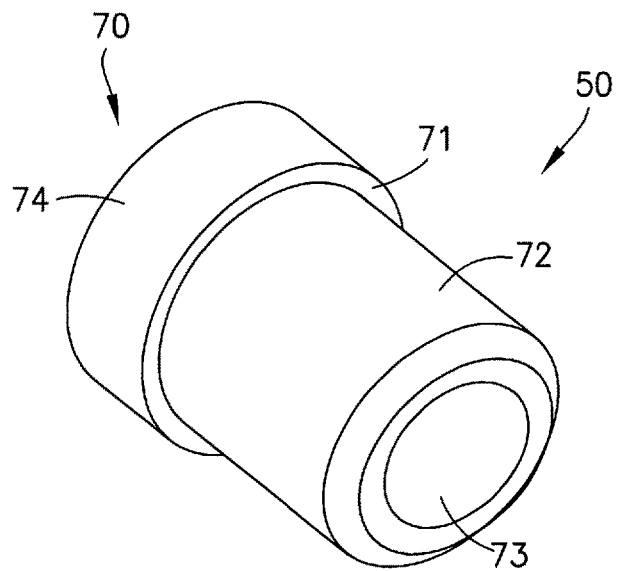
FIG. 6A is a perspective view of a sterility enhanced closure element in accordance with another embodiment.
Figure 6B:
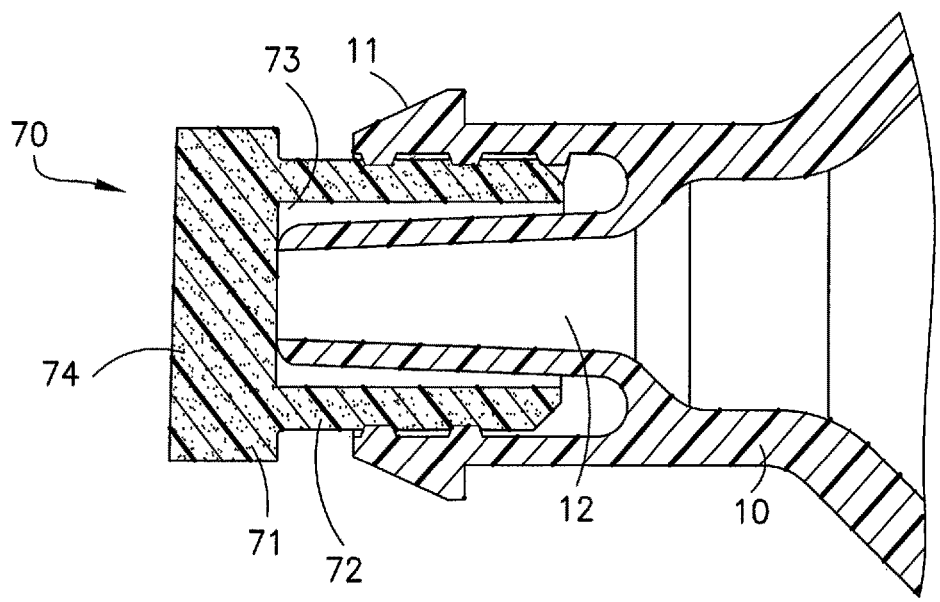
FIG. 6B is a cross-sectional view of the sterility enhanced closure element shown in FIG. 6A in use with a syringe.
Figure 7A:
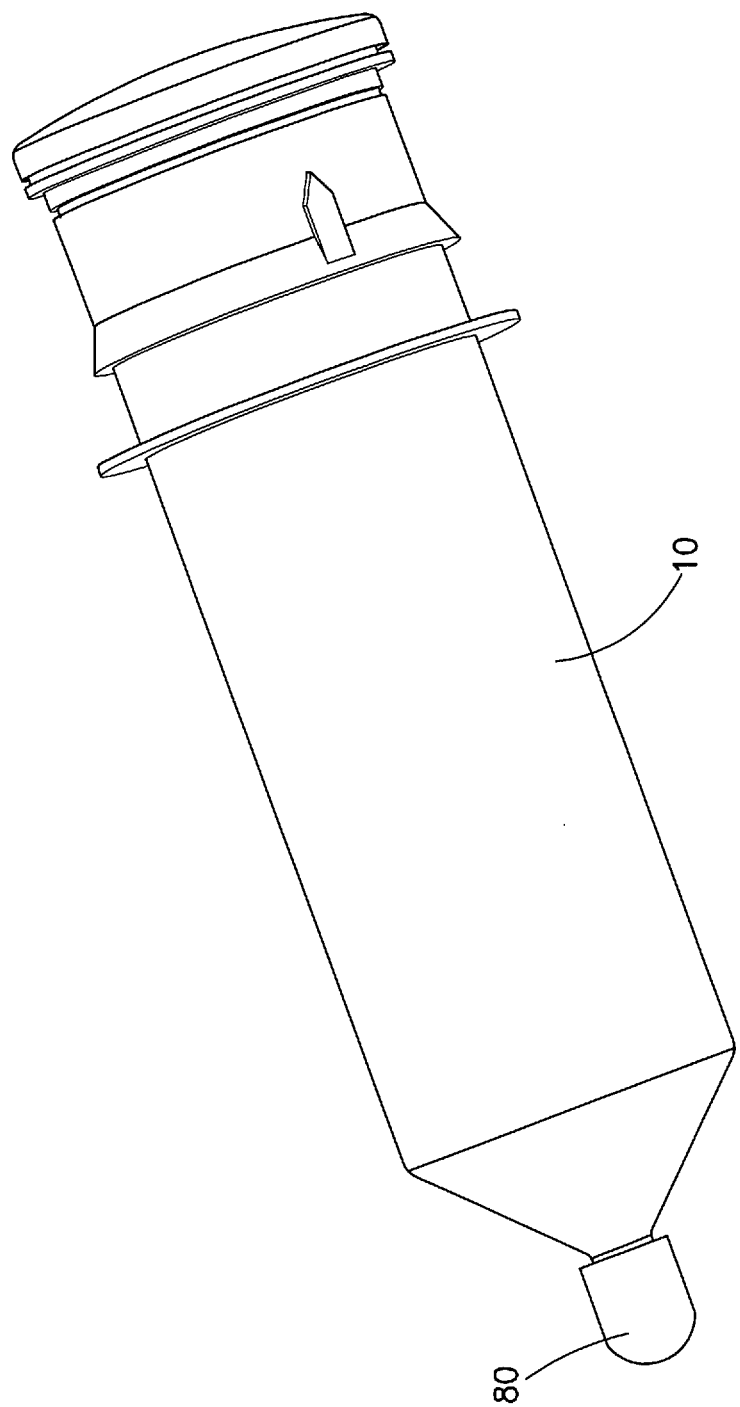
FIG. 7A is a perspective view of a sterility enhanced closure element in accordance with another embodiment shown in use with a syringe.
Figure 7B:
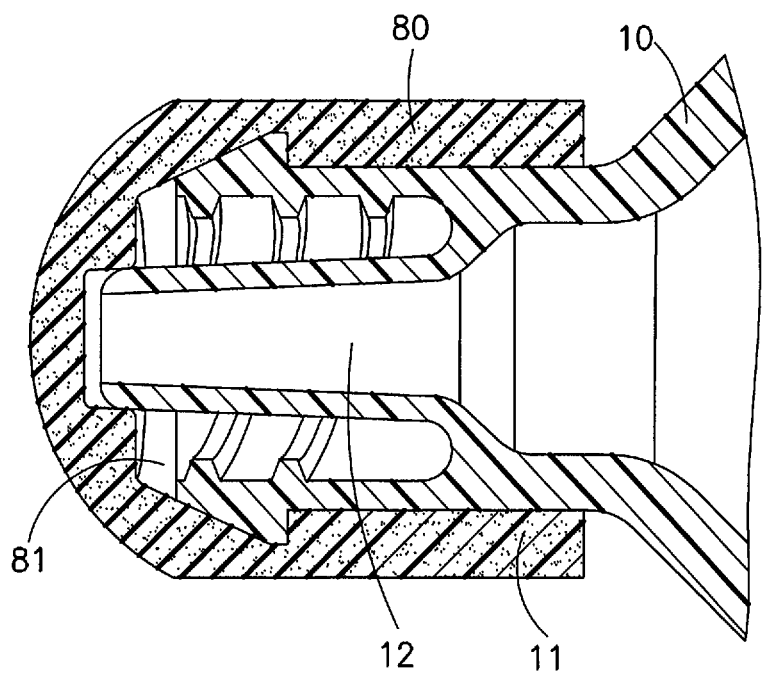
FIG. 7B is a cross-sectional view of the closure element shown in FIG. 7A.
Figure 7E:
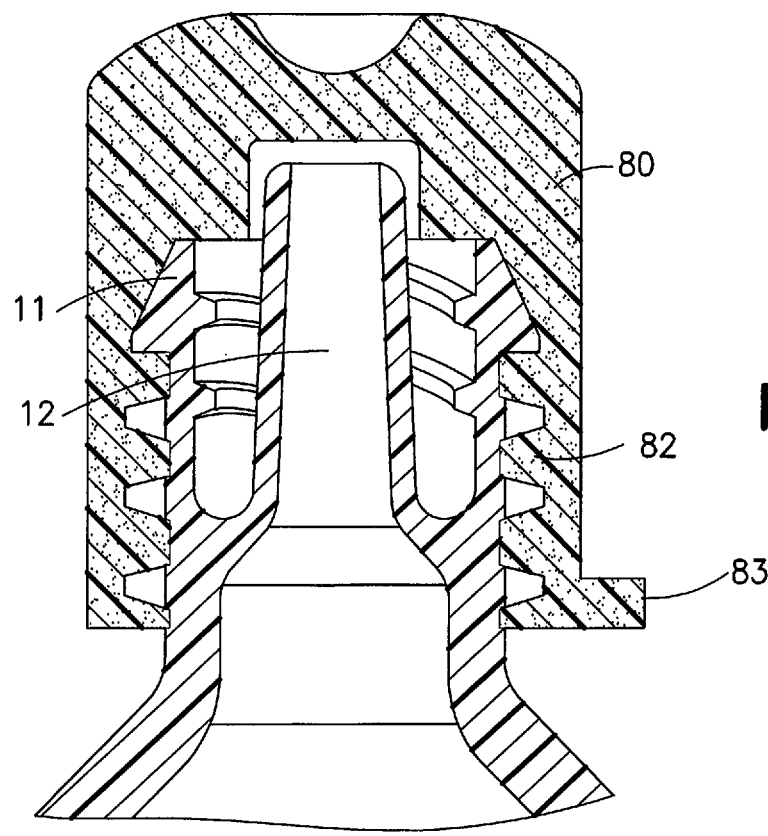
FIG. 7E a cross-sectional view of the closure element shown in FIG. 7C in use with a syringe.
Figure 7C:
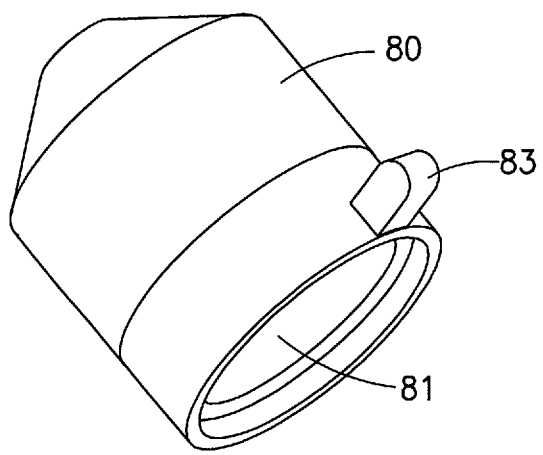
FIG. 7C is a perspective view of a closure element shown in accordance with another embodiment.
Figure 7D:
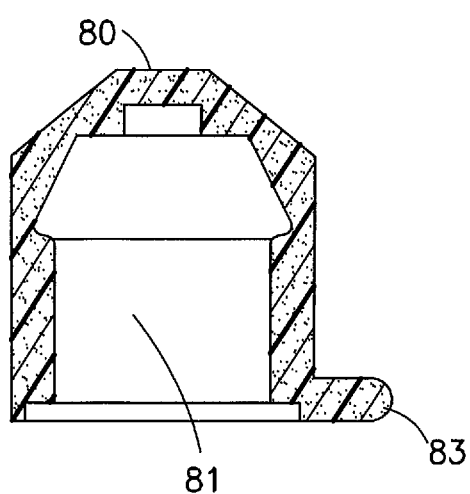
FIG. 7D is a cross-sectional view of the closure element shown in FIG. 7C.

FIGS. 6A-6B illustrate a closure element 70 in accordance with another embodiment of the present disclosure. The closure element 70 includes a body 74 configured as a cap with an enlarged distal portion 71, which is disposed outside of the discharge outlet 11 of the syringe 10, and a proximal portion 72. The distal portion 71 is configured to be grasped to remove the closure element 70 from the discharge outlet 11. The proximal portion 72 is configured to be received within the discharge outlet 11, which may be configured as a luer thread outlet, and is configured with a taper to form a luer engagement with the discharge outlet 11 and deform around the threads of the discharge outlet 11 in order to prevent accidental removal or displacement of the closure element 70. The proximal portion 72 includes an internal cavity 73 that receives the fluid path 12 such that the closure element 70 protects the fluid path 12 and maintains its sterility.

The closure element 70 is made from a press-formed polyethylene material that is made porous such that air is able to pass through the body of the closure element, but a tortuous path is formed that prevents passage of pathogens through the closure element 70 and the sterility of the fluid path is maintained. The use of a porous material, such as the press-formed polyethylene material, forms a complex inner geometry of the body 74 to allow venting of excess pressure within the syringe. The inner geometry of the body 74 is also tortuous enough to prevent pathogens from entering the fluid path 12 and compromising the sterility of the connection. By venting the excess pressure built up within the body of the syringe 10, the closure element 70 ensures that the plunger of the syringe 10 does not move due to changes in barometric pressure from thermal expansion or due to pressure buildup during an automatic advancement of a piston/ plunger assembly in an automated fluid injector when the closure element 70 is still installed. The closure element 70 may be left on the syringe 10 while the syringe 10 is loaded in the fluid injector and the auto forward function is engaged to maintain the sterility of the discharge outlet 11 at all times prior to removing the closure element 70 and connecting the discharge outlet 11 with a patient fluid path set.

FIGS. 7A-7E illustrate a closure element 80 in accordance with another embodiment of the present disclosure. The closure element 80 is in the form of a thermoplastic elastomer (TPE) or thermoplastic polyurethane (TPU) designed rubber cap, which is disposed over the discharge outlet 11 of the syringe 10. The closure element 80 includes an internal cavity 81 that is configured to conform to the shape of the discharge outlet 11 and the fluid path 12 so that the closure element 80 covers and protects the fluid path 12 to maintain its sterility. The closure element 80 and the syringe 10 may be treated after assembly such that the material of the closure element 80 becomes crosslinked or bonded to the exterior of the discharge outlet 11. The closure element 80 may include internal features, such as corrugations 82, to promote such a bond. The closure element 80 is configured to be ripped or torn off of the discharge outlet 11 so that the closure element 80 is tamper evident and secure during transport. To that end, the closure element 80 may be provided with a pull tab 83 (shown in FIGS. 7C-7E) to be grasped in order to remove the closure element 80 from the discharge outlet 11. The material and configuration of the closure element 80 are configured such that the closure element 80 is compliant in order to withstand changes in environmental pressure during shipment and so that accidental first action from a piston disposed within the syringe 10 would be absorbed. The closure element 80 may be formed from a colored resin, such as a red resin, to warn the user that the closure element 80 must be removed prior to use.

Figure 8A:
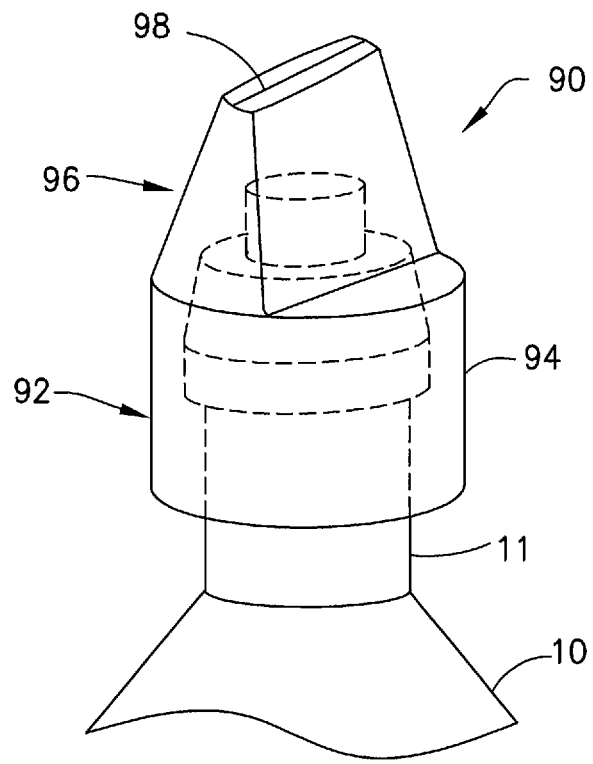
FIG. 8A is a perspective view of a sterility enhanced closure element in accordance with another embodiment.

FIGS. 8A-8D illustrate various other closure elements in accordance with separate embodiments of the present disclosure that are configured to snap onto or otherwise mechanically engage the discharge outlet of a syringe in order to protect the fluid path of the syringe and maintain its sterility. The closure elements may be formed of a compliant material, such as rubber. FIG. 8A shows a closure element 90 having a duck bill vent configuration such that air from the syringe 10 is able to pass through the vent to accommodate changes of pressure in the syringe 10 and/or movement of the piston/plunger, but pathogens cannot enter through the closure element 90. The closure element 90 includes a body 94 having a proximal portion 92 configured to be received around the discharge outlet 11, which may be configured as a luer thread outlet, and is configured with a taper to form a luer engagement with the discharge outlet 11 and deform around the threads of the discharge outlet 11 in order to prevent accidental removal or displacement of the closure element 90. The distal portion 96 includes a vent 98 that allows air from the syringe 10 to pass through the vent 98 to accommodate changes of pressure in the syringe 10 and/or movement of the piston/plunger, but does not allow pathogens to enter through the vent 98.

Figure 8B:
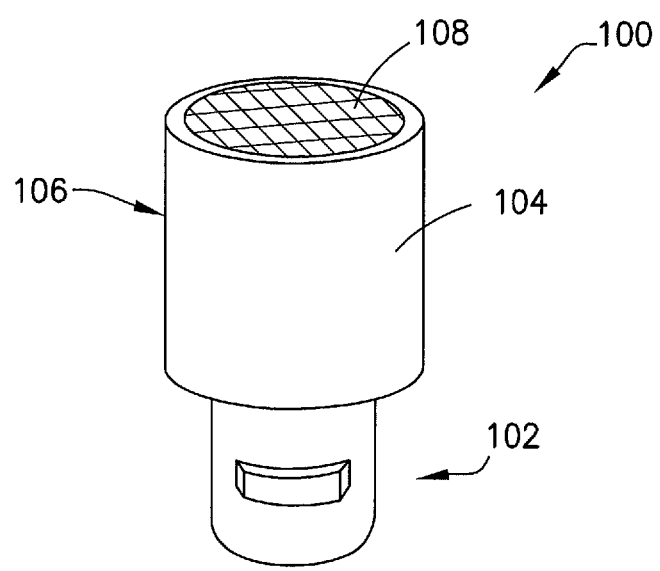
FIG. 8B is a perspective view of a sterility enhanced closure element in accordance with another embodiment.

FIG. 8B illustrates a closure element 100 formed from sintered polyethylene that engages the discharge outlet 11 of the syringe 10 that protects and maintains the sterility of the fluid path 12. The closure element 100 includes a body 104 having a proximal portion 102 configured to be received around the discharge outlet 11, which may be configured as a luer thread outlet, and is configured with a taper to form a luer engagement with the discharge outlet 11 and deform around the threads of the discharge outlet 11 in order to prevent accidental removal or displacement of the closure element 100. The distal portion 106 includes a vent 108 that allows air from the syringe 10 to pass through the vent 108 to accommodate changes of pressure in the syringe 10 and/or movement of the piston/plunger, but does not allow pathogens to enter through the vent 108.

Figure 8C:
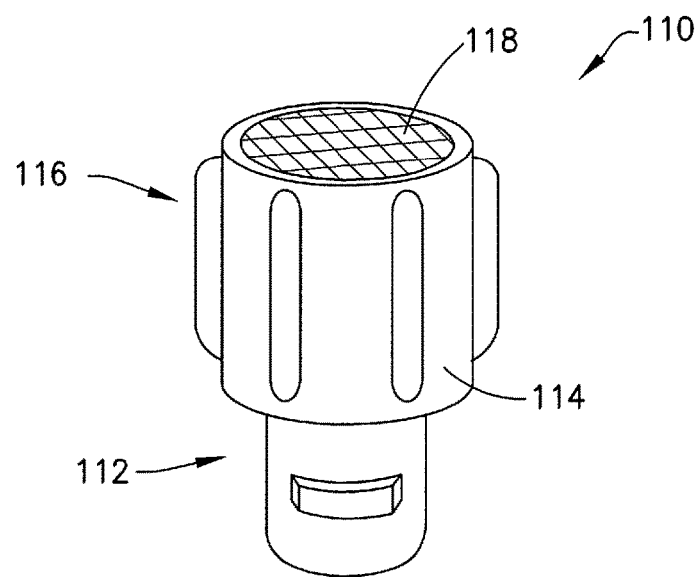
FIG. 8C is a perspective view of a sterility enhanced closure element in accordance with another embodiment.

FIG. 8C illustrates a closure element 110 formed as an insert of sintered polyethylene that engages the discharge outlet 11 of the syringe 10 that protects and maintains the sterility of the fluid path 12. The closure element 110 includes a body 114 having a proximal portion 112 configured to be received around the discharge outlet 11, which may be configured as a luer thread outlet, and is configured with a taper to form a luer engagement with the discharge outlet 11 and deform around the threads of the discharge outlet 11 in order to prevent accidental removal or displacement of the closure element 110. The distal portion 116 includes a vent 118 that allows air from the syringe 10 to pass through the vent 118 to accommodate changes of pressure in the syringe 10 and/or movement of the piston/ plunger, but does not allow pathogens to enter through the vent 118. The closure element 110 includes raised features 111 molded therein to assist in grasping the closure element 110 for removal from the discharge outlet 11 of the syringe 10. Alternatively, the raised features 111 may be formed as depressions that extend radially inward into the body 114. In either embodiment, the raised features 111 provide a grasping surface to facilitate the removal of the closure element 110 from the discharge outlet 11 of the syringe 10. The raised features 111, and/or the surface surrounding the raised features 111, may be textured to provide an increased frictional interface with the user's fingers during removal of the closure element 110.

Figure 8D:
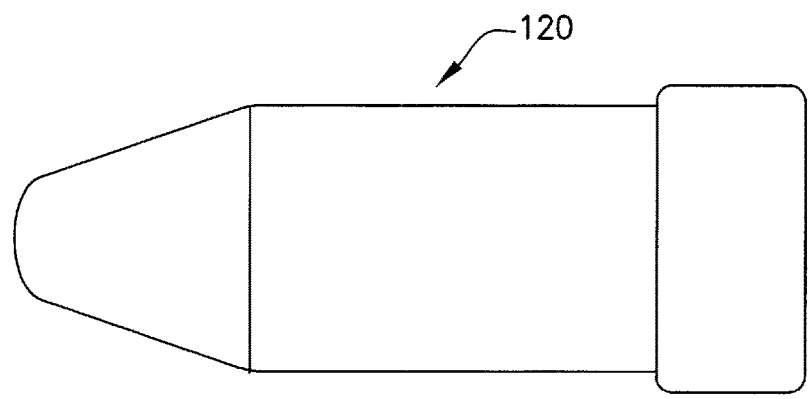
FIG. 8D is a perspective view of a sterility enhanced closure element in accordance with another embodiment.

FIG. 8D illustrates a closure element 120 formed from sintered polyethylene that can be inserted in the fluid path 12 of the syringe 10 to protect and maintain the sterility of the fluid path 12. In any of the embodiments shown in FIGS. 8A-8D, the closure element is made from a press-formed polyethylene material that is made porous such that air is able to pass through the body of the closure element, but a tortuous path is formed that prevents passage of pathogens through the closure element and the sterility of the fluid path is maintained. The use of a porous material, such as the press-formed polyethylene material, forms a complex inner geometry of the body of the closure element to allow venting of excess pressure within the syringe. The inner geometry of the closure element is also tortuous enough to prevent pathogens from entering the fluid path 12 and compromising the sterility of the connection. By venting the excess pressure built up within the body of the syringe 10, the closure element ensures that the plunger of the syringe 10 does not move due to changes in barometric pressure from thermal expansion or due to pressure buildup during an automatic advancement of a piston/plunger assembly in an automated fluid injector when the closure element is still installed. The closure element may be left on the syringe 10 while the syringe 10 is loaded in the fluid injector and the auto forward function is engaged to maintain the sterility of the discharge outlet 11 at all times prior to removing the closure element and connecting the discharge outlet 11 with a patient fluid path set.

FIGS. 9A-9D illustrate a closure element 130 in accordance with another embodiment of the present disclosure. The closure element 130 includes a body 134 having a proximal portion 132 configured to be received around the discharge outlet 11, which may be configured as a luer thread outlet, and is configured with a taper to form a luer engagement with the discharge outlet 11 and deform around the threads of the discharge outlet 11 in order to prevent accidental removal or displacement of the closure element 130.

Figure 9A:
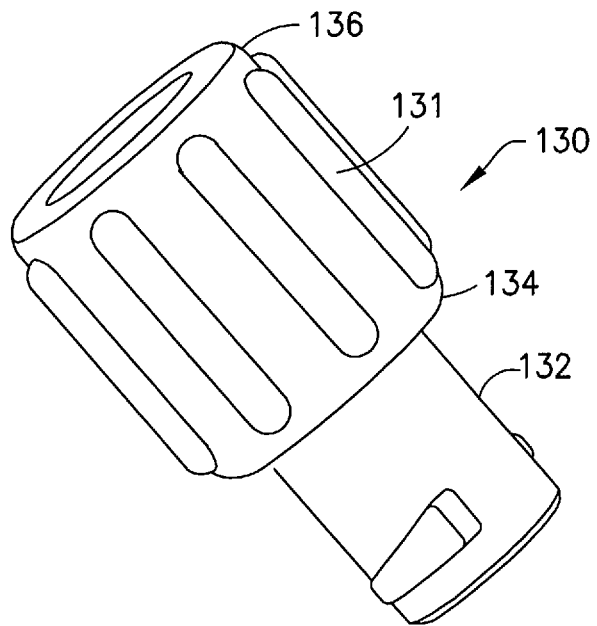
FIG. 9A is a perspective view of a sterility enhanced closure element in accordance with another embodiment.
Figure 9B:
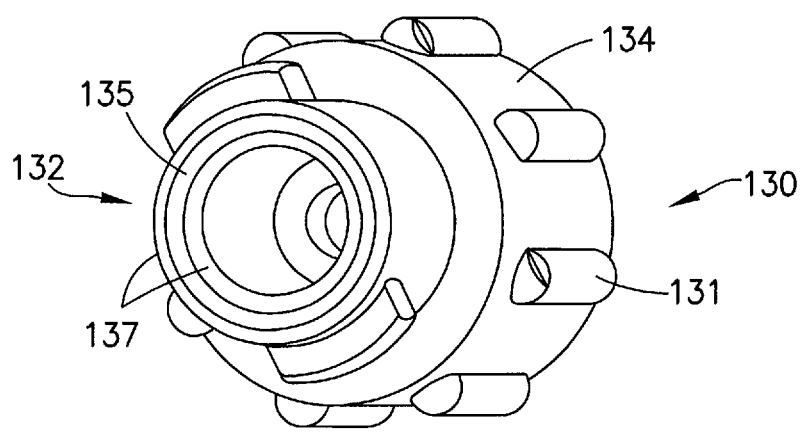
FIG. 9B is a perspective view of a proximal portion of the closure element shown in FIG. 9A.
Figure 9C:
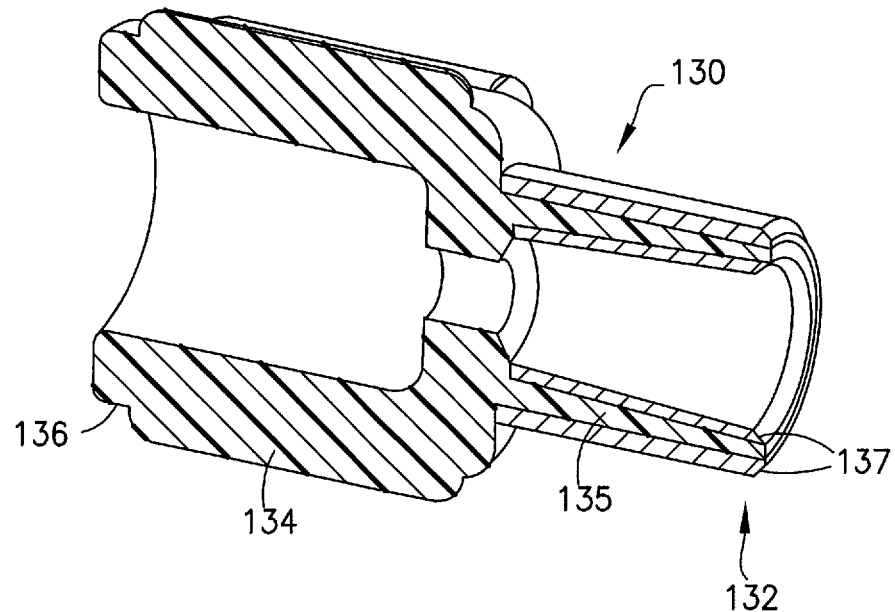
FIG. 9C is a cross-sectional view of the closure element shown in FIG. 9A.
Figure 9D:
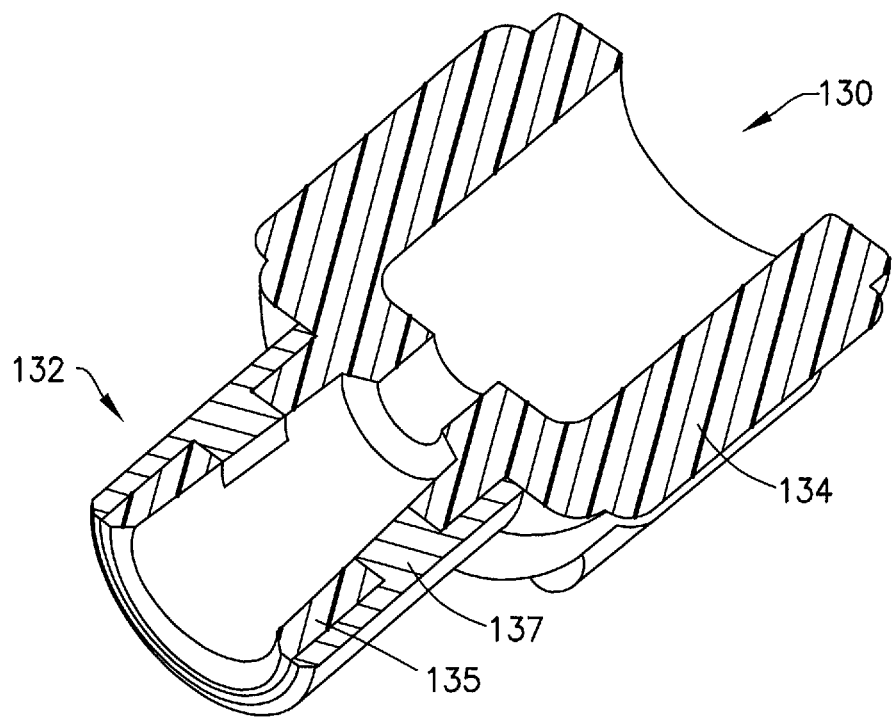
FIG. 9D is a cross-sectional view of the closure element in accordance with another embodiment.

With reference to FIGS. 9C-9D, the proximal portion 132 includes a substrate 135 that is at least partially surrounded with a jacket 137. The jacket 137 may completely envelop the substrate 135 on the inside and outside portions of the substrate 135 (FIG. 9C), or the jacket 137 may only partially extend on one or both of the inside and outside portions of the substrate 135 (FIG. 9D). In one embodiment, the closure element 130, including the substrate 135, is made from a thermoplastic material, such as polypropylene or polycarbonate. The jacket 137 is made from a different material to that of the substrate 135. In various embodiments, the jacket 135 is made from TPE (thermoplastic elastomer), TPU (thermoplastic polyurethane), TPV (thermoplastic vulcanizates), OBC (olefin block copolymer), or silicone. The jacket 137 is molded over the substrate 135. Desirably, the material from which the jacket 137 is made has a chemical affinity for the material from which the substrate 135 is made, such that a chemical bond is formed adhering the two materials together. In another embodiment, mechanical interlock features may be added to hold the materials together if the chemical adhesion is weak or nonexistent, or to supplement the chemical adhesion of the two materials.

The body 134 also has a distal portion 136 having one or more raised features 131 molded thereon to assist in grasping the closure element 130 for removal from the discharge outlet 11 of the syringe 10. Alternatively, the raised features 131 may be formed as depressions that extend radially inward into the body 134. In either embodiment, the raised features 131 provide a grasping surface to facilitate the removal of the closure element 130 from the discharge outlet 11 of the syringe 10. The raised features 131, and/or the surface surrounding the raised features 131, may be textured to provide an increased frictional interface with the user's fingers during removal of the closure element 130.

The use of a disparate material on the jacket 137 to that of the substrate 135 of the proximal portion 132 of the closure element 130 enables the closure element 130 to have, for example, increased friction with the discharge outlet 11 of the syringe 10 so that the closure element 130 may be installed with less torque, thereby imparting less stress onto the discharge outlet 11. The reduction in torque reduces the incidence of ESC (environmental stress cracking) and maintains the connection between the closure element 130 and the discharge outlet 11.

Figure 10A:
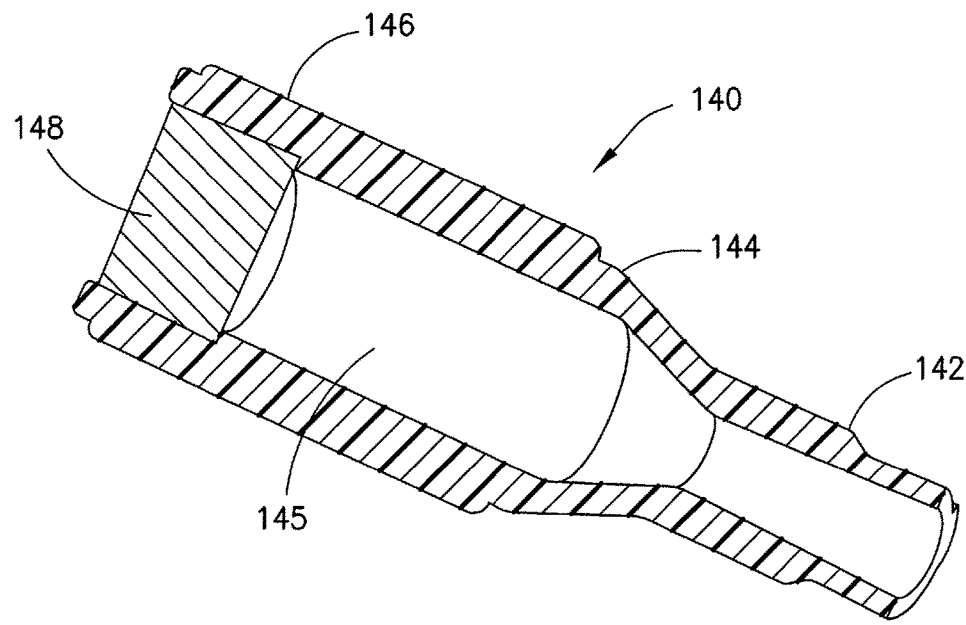
FIG. 10A is a perspective view of a sterility enhanced closure element in accordance with another embodiment.
Figure 10B:
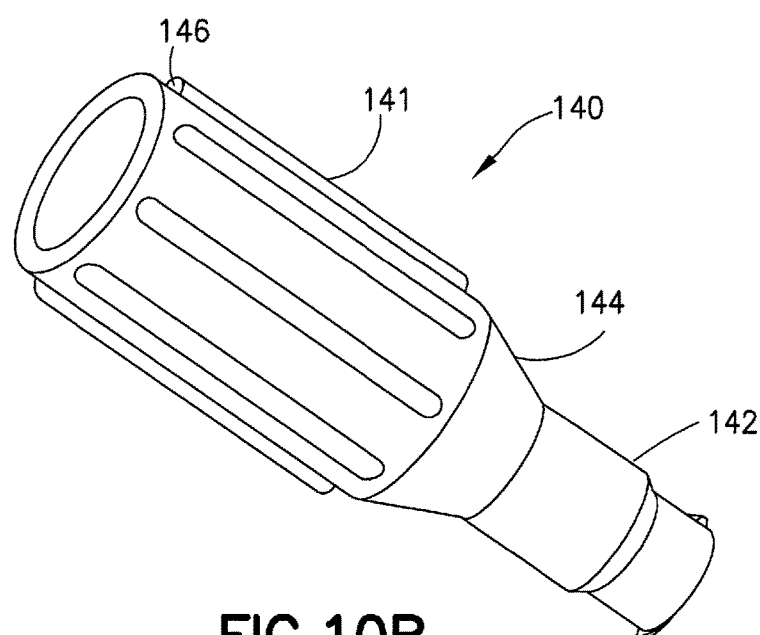
FIG. 10B is a cross-sectional view of the closure element shown in FIG. 10A.

FIGS. 10A-10B illustrate a closure element 140 formed as an insert that engages the discharge outlet 11 of the syringe 10 that protects and maintains the sterility of the fluid path 12. The closure element 140 includes a body 144 having a proximal portion 142 configured to be received around the discharge outlet 11, which may be configured as a luer thread outlet, and is configured with a taper to form a luer engagement with the discharge outlet 11 and deform around the threads of the discharge outlet 11 in order to prevent accidental removal or displacement of the closure element 140. The distal portion 146 includes a vent 148 that allows air from the syringe 10 to pass through the vent 148 to accommodate changes of pressure in the syringe 10 and/or movement of the piston/plunger, but does not allow pathogens to enter through the vent 148. An internal volume 145 is formed within the interior of the closure element 140 to provide an expansion space for receiving fluid during priming of the fluid injection system. In one embodiment, the internal volume 145 is dimensioned to receive a volume of fluid expelled from the syringe 10 during a typical priming operation (~1 ml). In this manner, the closure element 140 may be left on the syringe 10 during a priming operation to maintain the sterility of the discharge outlet 11.

The closure element 140 includes raised features 141 molded therein to assist in grasping the closure element 140 for removal from the discharge outlet 11 of the syringe 10. Alternatively, the raised features 141 may be formed as depressions that extend radially inward into the body 144. In either embodiment, the raised features 141 provide a grasping surface to facilitate the removal of the closure element 140 from the discharge outlet 11 of the syringe 10. The raised features 141, and/or the surface surrounding the raised features 141, may be textured to provide an increased frictional interface with the user's fingers during removal of the closure element 140.

While embodiments of a sterility enhanced closure for a fluid path set and methods of operation thereof were provided in the foregoing description, those skilled in the art may make modifications and alterations to these embodiments without departing from the scope and spirit of the disclosure. Accordingly, the foregoing description is intended to be illustrative rather than restrictive. The disclosure described hereinabove is defined by the appended claims and all changes to the disclosure that fall within the meaning and the range of equivalency of the claims are to be embraced within their scope.

The disclosure claimed is:

1. A syringe assembly comprising:
    a syringe having a body with a proximal end and a distal end;
    a discharge outlet formed at the distal end of the syringe, wherein the discharge outlet comprises a luer connector having one or more internal threads;
    a closure element having a body having a distal portion and a proximal portion configured for removable engagement with at least a portion of the discharge outlet;
    at least one engagement feature on the proximal portion of the body of the closure element for engaging the luer connector on the discharge outlet; and
    at least one crush rib extending radially outward from the at least one engagement feature and configured to engage the one or more internal threads of the luer connector,
    wherein the proximal portion of the body of the closure element has a substrate made from a first material and a jacket made from a second material, and
    wherein the body of the closure element is porous to define a tortuous internal path through the body of the closure element to allow venting of excess pressure within the syringe such that a plunger of the syringe does not move due to changes in barometric pressure while preventing pathogens from entering the syringe.

2. The syringe assembly of claim 1, wherein the body of the closure element has at least one raised or recessed element to assist in grasping the closure element during removal of the closure element from the discharge outlet.

3. The syringe assembly of claim 1, wherein the closure element is made from a polypropylene material.

4. The syringe assembly of claim 3, wherein the polypropylene material is press-formed.

5. A closure element for a discharge outlet of a syringe, the closure element comprising:

a body having a distal portion and a proximal portion configured for removable engagement with at least a portion of a discharge outlet of a syringe;

at least one engagement feature on the proximal portion of the body for engaging a luer connector on the discharge outlet; and at least one crush rib extending radially outward from the at least one engagement feature and configured to engage one or more internal threads of the luer connector, wherein the proximal portion of the body has a substrate made from a first material and a jacket made from a second material, and wherein the body is porous to define a tortuous internal path through the body to allow venting of excess pressure within the syringe such that a plunger of the syringe does not move due to changes in barometric pressure while preventing pathogens from entering the syringe.

6. The closure element of claim 5, further comprising a vent extending through at least a portion of the body to allow the venting of excess pressure within the syringe.

7. The closure element of claim 5, wherein the body has at least one raised or recessed element to assist in grasping the closure element during removal of the closure element from the discharge outlet of the syringe.

8. The closure element of claim 5, wherein the closure element is made from a polypropylene material.

9. The closure element of claim 8, wherein the polypropylene material is press-formed.

10. The closure element of claim 5, wherein the first material is different from the second material.

11. The closure element of claim 5, wherein the jacket is molded over the substrate to envelop at least a portion of the substrate.

12. The closure element of claim 5, wherein the tortuous internal path comprises a vent extending through at least a portion of the substrate to allow the venting of excess pressure within the syringe while preventing pathogens from entering the syringe.

13. The closure element of claim 5, wherein at least the first material of the closure element is a polypropylene material.

14. The closure element of claim 13, wherein the polypropylene material is press-formed.

* * * * *